US011992745B2

(12) United States Patent
Kulangara Muriyil et al.

(10) Patent No.: US 11,992,745 B2
(45) Date of Patent: May 28, 2024

(54) METHOD AND SYSTEM FOR ASSESSING AND IMPROVING WELLNESS OF PERSON USING BODY GESTURES

(71) Applicant: Tata Consultancy Services Limited, Mumbai (IN)

(72) Inventors: Robin Tommy Kulangara Muriyil, Thiruvananthapuram (IN); Athira Krishnan, Thiruvananthapuram (IN); Vishnu Sivan, Thiruvananthapuram (IN); Monishaa Prabhakar, Thiruvananthapuram (IN); Reshmi Ravindranathan, Thiruvananthapuram (IN); Anandu Sugathan, Thiruvananthapuram (IN); Balakumar Kanagasabapathy, Tamilnadu (IN)

(73) Assignee: Tata Consultancy Services Limited, Mumbai (IN)

( * ) Notice: Subject to any disclaimer, the term of this patent is extended or adjusted under 35 U.S.C. 154(b) by 7 days.

(21) Appl. No.: 17/816,312

(22) Filed: Jul. 29, 2022

(65) Prior Publication Data

US 2023/0106401 A1    Apr. 6, 2023

(30) Foreign Application Priority Data

Sep. 2, 2021   (IN) .............................. 202121039878

(51) Int. Cl.
*A63B 71/06* (2006.01)
*G06T 7/20* (2017.01)
(Continued)

(52) U.S. Cl.
CPC ............ *A63B 71/0622* (2013.01); *G06T 7/20* (2013.01); *G06T 7/70* (2017.01); *G06V 10/751* (2022.01);
(Continued)

(58) Field of Classification Search
CPC ...... A63B 71/0622; G06T 7/70; G06V 40/10; G06V 10/751; G06V 40/20
See application file for complete search history.

(56) References Cited

U.S. PATENT DOCUMENTS 6,749,432 B2 *   6/2004   French ............... G09B 19/0038
                                                         434/362
7,292,151 B2 *   11/2007  Ferguson .............. A63F 13/211
                                                         340/407.1
(Continued)

OTHER PUBLICATIONS

Fernández de Dios, Pablo, "Key body pose detection and movement assessment of fitness performances" Computer Science, Date: 2015, Publisher: Semantics Scholar, https://repository.lboro.ac.uk/articles/thesis/Key_body_pose_detection_and_movement_assessment_of_fitness_performances/9407045.
(Continued)

*Primary Examiner* — Xuan M Thai
*Assistant Examiner* — Sadaruz Zaman
(74) *Attorney, Agent, or Firm* — Finnegan, Henderson, Farabow, Garrett & Dunner, LLP

(57) ABSTRACT

Good health is one of the paramount essentials for any human being. A method and system for assessing and improving wellness of a person using body gestures have been provided. The system is configured to address fitness, wellness and physical movement related problems for both the abled and the differently abled society. The disclosure provides an intelligent and adaptive system that will comprehend the gestures and postures of the person to assess his capability of undertaking wellness activities. The person's movement capabilities and the environment are learnt by the system to track the gestures for the activities. Based on his gestures, the extent of activity achievement is calculated. The system also has the feature of provisioning dynamic activities to the person based on prior attempts and levels of
(Continued)

achievements. Additionally, the system also providing the fitness routine in an AR environment by human-to-object mapping through object detection and augmentation.

11 Claims, 6 Drawing Sheets

(51) Int. Cl.
    *G06T 7/70*         (2017.01)
    *G06V 10/75*      (2022.01)
    *G06V 40/10*      (2022.01)
    *G06V 40/20*      (2022.01)
    *G16H 10/20*      (2018.01)

(52) U.S. Cl.
    CPC ............. *G06V 40/10* (2022.01); *G06V 40/20* (2022.01); *A63B 2071/065* (2013.01); *A63B 2214/00* (2020.08); *A63B 2220/05* (2013.01); *A63B 2220/807* (2013.01); *G06T 2207/20081* (2013.01); *G06T 2207/30196* (2013.01); *G06T 2207/30241* (2013.01); *G16H 10/20* (2018.01)

(56) References Cited

U.S. PATENT DOCUMENTS

| | | | | |
|---|---|---|---|---|
| 8,092,355 | B2 * | 1/2012 | Mortimer | A63B 26/003 |
| | | | | 482/148 |
| 8,847,988 | B2 * | 9/2014 | Geisner | A63B 71/00 |
| | | | | 345/633 |
| 10,839,954 | B2 * | 11/2020 | Flavell | G16H 20/30 |
| 10,945,641 | B2 * | 3/2021 | Mirelman | A61B 5/369 |
| 11,030,918 | B2 * | 6/2021 | Wallach | G09B 19/0038 |
| 11,620,857 | B2 * | 4/2023 | Masui | A61B 5/1128 |
| | | | | 382/103 |
| 11,633,659 | B2 * | 4/2023 | Virkar | G06T 13/40 |
| | | | | 345/633 |
| 11,819,734 | B2 * | 11/2023 | Lee | A63B 24/0021 |
| 2014/0188009 | A1 * | 7/2014 | Lange | A61B 5/1127 |
| | | | | 600/595 |
| 2017/0076619 | A1 * | 3/2017 | Wallach | G09B 19/0038 |
| 2017/0136296 | A1 * | 5/2017 | Barrera | G16H 20/30 |
| 2020/0396411 | A1 * | 12/2020 | Hattori | G06V 40/10 |
| 2022/0072377 | A1 * | 3/2022 | Russell | G06V 10/25 |
| 2022/0198368 | A1 * | 6/2022 | May | G06Q 10/063112 |
| 2022/0280837 | A1 * | 9/2022 | Håkansson | G06T 7/70 |
| 2022/0366811 | A1 * | 11/2022 | Donnelly | G09B 5/14 |
| 2023/0106401 | A1 * | 4/2023 | Kulangara Muriyil | ...... |
| | | | | G06V 40/10 |
| 2023/0285832 | A1 * | 9/2023 | Masiukiewicz | G06V 40/10 |

OTHER PUBLICATIONS

Stroulia, Eleni et al., "Virtual Gym: aiding older adults with exercise compliance through serious gameplay", Well Springs, Date: Jul. 2020, Publisher: Ualberta, https://www.ualberta.ca/kinesiology-sport-recreation/media-library/research/centres-and-units/centre-for-active-living/wellspring/2020/2020_july.pdf.

Indian Patent Application No. 201921035264A filed Sep. 2, 2019, Inventor Jitendra Agrawal et al. for System and Method for Real-Time Assessment and Guidance On Exercise Posture, 23 pages.

* cited by examiner

METHOD AND SYSTEM FOR ASSESSING AND IMPROVING WELLNESS OF PERSON USING BODY GESTURES

PRIORITY CLAIM

This U.S. patent application claims priority under 35 U.S.C. § 119 to: Indian Patent Application No. 202121039878, filed on 2 Sep. 2021. The entire contents of the aforementioned application are incorporated herein by reference.

TECHNICAL FIELD

The disclosure herein generally relates to the field of human gesture analysis and, more particularly, to a method and system for assessing and improving wellness of person using body gestures.

BACKGROUND

Good health is one of the paramount essentials for any human being. Every human being works towards maintaining their health in several ways. Usually, the users depend on the gymnasium (gyms) and personal trainers to carry out the fitness workouts. In the absence of personal trainers, the users do not have an option to receive feedback on the progress. More so, in pandemic or lockdown situation, the closure of the gyms has led to the workouts being carried out at the homes. But the lack of real-time monitoring of the user actions, personalized instructions and guidance to the user will impact the effectiveness of the workout.

In case of the differently abled society, many children and elderly population are completely limited to homes or bedridden and do not have the option to attend therapy at designated centers. Even at schools and clinics, they are subjected to traditional therapy methods that include massages, orthopedic hand manipulations, physiotherapy, occupational therapy et cetera. The process is entirely manual and dependent on a physiotherapist to understand the improvement.

There are also studies that indicate how the physical activity and healthcare costs are inter-related. In developed countries, this is even tied to the lower medical insurance premiums. Hence, it is imperative that the physical dependencies should be eliminated for a health regime to encourage more people to engage in fitness programs.

SUMMARY

Embodiments of the present disclosure present technological improvements as solutions to one or more of the above-mentioned technical problems recognized by the inventors in conventional systems. For example, in one embodiment, a system for assessing and improving wellness of person using body gestures is provided. The system comprises an input/output interface, a camera, one or more hardware processors and a memory. The input/output interface registers the person before the initiating the assessment, via one or more hardware devices, wherein the registering involves receiving a plurality of physical characteristics of the person. The camera for identifies a plurality of joints of the person, wherein the plurality of joints is used to track movement of the person within a frame of the camera. The memory in communication with the one or more hardware processors, wherein the one or more first hardware processors are configured to execute programmed instructions stored in the one or more first memories, to: guide the person to perform a first set of exercises, wherein the first set of exercises is used to identify a maximum possible reach around the person in all direction; select an exercise to be performed by the person; identify a set of validation points of the exercise for the person, wherein the identification of the set of validation points further comprises: training an algorithm using minimal data of a set of standard human joint variations with human joint information captured for a set of people without any obstacle around, computing joint variations for the set of people while performing the exercise using the trained algorithm, applying a plurality of obstacle bounds around to predict the joint variations with the plurality of obstacle bounds for the person, wherein the computed joint variations and the predicted joint variations with the plurality of obstacle bounds is referred as a simulated trajectory data, dividing the simulated trajectory based on, variation of the trajectory with respect to a pattern of motion while attempting the exercise and variation of the endpoint around an expected target position due to convenience, and utilizing end coordinate measures of the simulated data as the set of validation points; track a real time joint coordinates of the person; compare the real time joint coordinates of the person with the generated set of validation points, when the person performs the exercise; provide an alert to the person based on the comparison to complete the exercise in a predefined required manner; compute a percentage closeness achieved around each validation point amongst the set of validation points; calculate an average of the computed percentage closeness of all the validation points to compute a completion score of the exercise; and recommend a right way of doing the exercise, and a second set of exercise to the person based on the completion score and a set of predefined conditions.

In another aspect, a method for assessing and improving wellness of a person using body gestures is provided. Initially, the person is registered before initiating the assessment, wherein the registering involves receiving a plurality of physical characteristics of the person. In the next step, a plurality of joints of the person is identified using a camera, wherein the plurality of joints is used to track movement of the person within a frame of the camera. Further the person is guided to perform a first set of exercises, wherein the first set of exercises is used to identify a maximum possible reach around the person in all direction. An exercise is then selected to be performed by the person. Further, a set of validation points of the exercise is identified for the person, wherein the identification of the set of validation points further comprises: training an algorithm using minimal data of a set of standard human joint variations with human joint information captured for a set of people without any obstacle around, computing joint variations for the set of people while performing the exercise using the trained algorithm, applying a plurality of obstacle bounds around to predict the joint variations with the plurality of obstacle bounds for the person, wherein the computed joint variations and the predicted joint variations with the plurality of obstacle bounds is referred as a simulated trajectory data, dividing the simulated trajectory based on, variation of the trajectory with respect to a pattern of motion while attempting the exercise and variation of the endpoint around an expected target position due to convenience, and utilizing end coordinate measures of the simulated data as the set of validation points. In the next step, a real time joint coordinates of the person are tracked. The real time joint coordinates of the person are then compared with the generated set of validation points, when the person performs the exercise. In the next step, an alert is provided to the person based on the comparison to complete the exercise in a predefined required manner. Further a percentage closeness achieved around each validation point amongst the set of validation points is computed. Further, an average of the computed percentage closeness of all the validation points is computed to compute a completion score of the exercise. And finally, a right way of doing the exercise, and a second set of exercises are recommended to the person based on the completion score and a set of predefined conditions.

In yet another aspect, one or more non-transitory machine-readable information storage mediums comprising one or more instructions which when executed by one or more hardware processors cause assessing and improving wellness of a person using body gestures. Initially, the person is registered before initiating the assessment, wherein the registering involves receiving a plurality of physical characteristics of the person. In the next step, a plurality of joints of the person is identified using a camera, wherein the plurality of joints is used to track movement of the person within a frame of the camera. Further the person is guided to perform a first set of exercises, wherein the first set of exercises is used to identify a maximum possible reach around the person in all direction. An exercise is then selected to be performed by the person. Further, a set of validation points of the exercise is identified for the person, wherein the identification of the set of validation points further comprises: training an algorithm using minimal data of a set of standard human joint variations with human joint information captured for a set of people without any obstacle around, computing joint variations for the set of people while performing the exercise using the trained algorithm, applying a plurality of obstacle bounds around to predict the joint variations with the plurality of obstacle bounds for the person, wherein the computed joint variations and the predicted joint variations with the plurality of obstacle bounds is referred as a simulated trajectory data, dividing the simulated trajectory based on, variation of the trajectory with respect to a pattern of motion while attempting the exercise and variation of the endpoint around an expected target position due to convenience, and utilizing end coordinate measures of the simulated data as the set of validation points. In the next step, a real time joint coordinates of the person are tracked. The real time joint coordinates of the person are then compared with the generated set of validation points, when the person performs the exercise. In the next step, an alert is provided to the person based on the comparison to complete the exercise in a predefined required manner. Further a percentage closeness achieved around each validation point amongst the set of validation points is computed. Further, an average of the computed percentage closeness of all the validation points is computed to compute a completion score of the exercise. And finally, a right way of doing the exercise, and a second set of exercises are recommended to the person based on the completion score and a set of predefined conditions.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
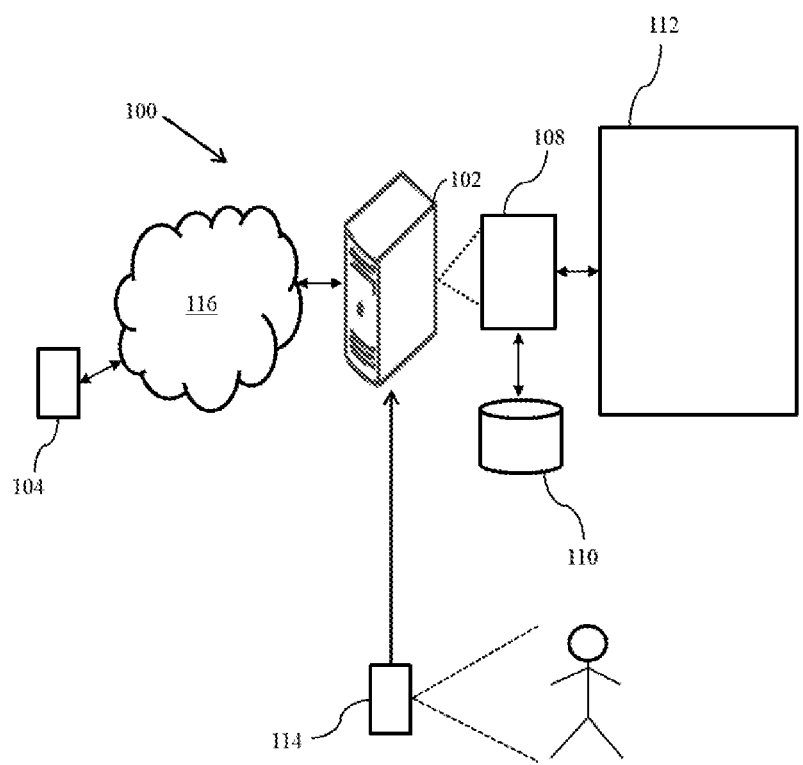
FIG. 1 illustrates a network diagram of a system for assessing and improving wellness of person using body gestures according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Good health is one of the paramount essentials for a person. Every person works towards maintaining their health in several ways. Usually, the users depend on the gymnasium (gyms) and personal trainers to carry out the fitness workouts. In the absence of personal trainers, the users do not have an option to receive feedback on the progress. But the lack of real-time monitoring of the user actions, personalized instructions and guidance to the user will impact the effectiveness of the workout.

There are also a lot of mobile and web-based applications that would provide fitness workouts, but these applications are not capable of guiding the person in doing the workout as they only provide some demonstration videos. Few of the interactive applications are also present in the prior art for guiding the person for performing the exercises. They all require extra device to be attached to the body to understand moving or not. This results in the restriction of freedom of movement of the person and increase the overall cost of the setup.

The present disclosure provides a method and a system for assessing and improving wellness of a person using body gestures. The system is configured to address fitness, wellness and physical movement related problems for both the abled and the differently abled society. The disclosure provides an intelligent and adaptive system that will comprehend the gestures and postures of the person to assess his capability of undertaking wellness activities. The person's movement capabilities and the environment are learnt by the system to track the gestures for the activities. Based on person gestures, the extent of activity achievement is calculated. The activities are developed to be adaptive based on the person's environment, physical conditions as well as movement capabilities. The system also has the feature of provisioning dynamic activities to the person based on person's prior attempts and levels of achievements. Additionally, the system is defining a new way to doing the fitness routine in an augmented reality (AR) environment by human-to-object mapping through object detection and augmentation.

Referring now to the drawings, and more particularly to FIG. 1 through FIG. 6, where similar reference characters denote corresponding features consistently throughout the figures, there are shown preferred embodiments and these embodiments are described in the context of the following exemplary system and/or method.

According to an embodiment of the disclosure, a system 100 for assessing and improving wellness of a person using body gestures is shown in the network diagram of FIG. 1. The system 100 is configured to learn person's movement capabilities and surrounding environment to track the gestures for exercises performed by the person. The system is configured to understand person's gesture and posture and to calculate the percentage of activity achievement. The system 100 is capable of tracking the motion of the person within a frame of a camera present in front of the person. The motion includes forward, backward, sideward, and diagonal movements.

The person can perform intuitive and adaptive exercises based on the person's environment and his physical conditions. The system 100 is also configured to dynamically assign activity based on the person's attributes. The system 100 is also configured to detect any interactable object and based on the detection, activity can be dynamically assigned by combining the person and detected object.

Although the present disclosure is explained considering that the system 100 is implemented on a server, it may also be present elsewhere such as a local machine or an edge or cloud. It may be understood that the system 100 comprises one or more computing devices 102, such as a laptop computer, a desktop computer, a notebook, a workstation, a cloud-based computing environment and the like. It will be understood that the system 100 may be accessed through one or more input/output interfaces 104, collectively referred to as I/O interface 104. Examples of the I/O interface 104 may include, but are not limited to, a user interface, a portable computer, a personal digital assistant, a handheld device, a smartphone, a tablet computer, a workstation and the like. The I/O interface 104 is communicatively coupled to the system 100 through a network 106.

In an embodiment, the network 106 may be a wireless or a wired network, or a combination thereof. In an example, the network 106 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 106 may include a variety of network devices, including routers, bridges, servers, computing devices, storage devices. The network devices within the network 106 may interact with the system 100 through communication links.

The system 100 may be implemented in a workstation, a mainframe computer, a server, and a network server. In an embodiment, the computing device 102 further comprises one or more hardware processors 108, one or more memory 110, hereinafter referred as a memory 110 and a data repository 112, for example, a repository 112. The memory 110 is in communication with the one or more hardware processors 081, wherein the one or more hardware processors 108 are configured to execute programmed instructions stored in the memory 110, to perform various functions as explained in the later part of the disclosure. The repository 112 may store data processed, received, and generated by the system 100.

The system 100 supports various connectivity options such as BLUETOOTH®, USB, ZigBee and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. The components and functionalities of the system 100 are described further in detail.

Figure 2:
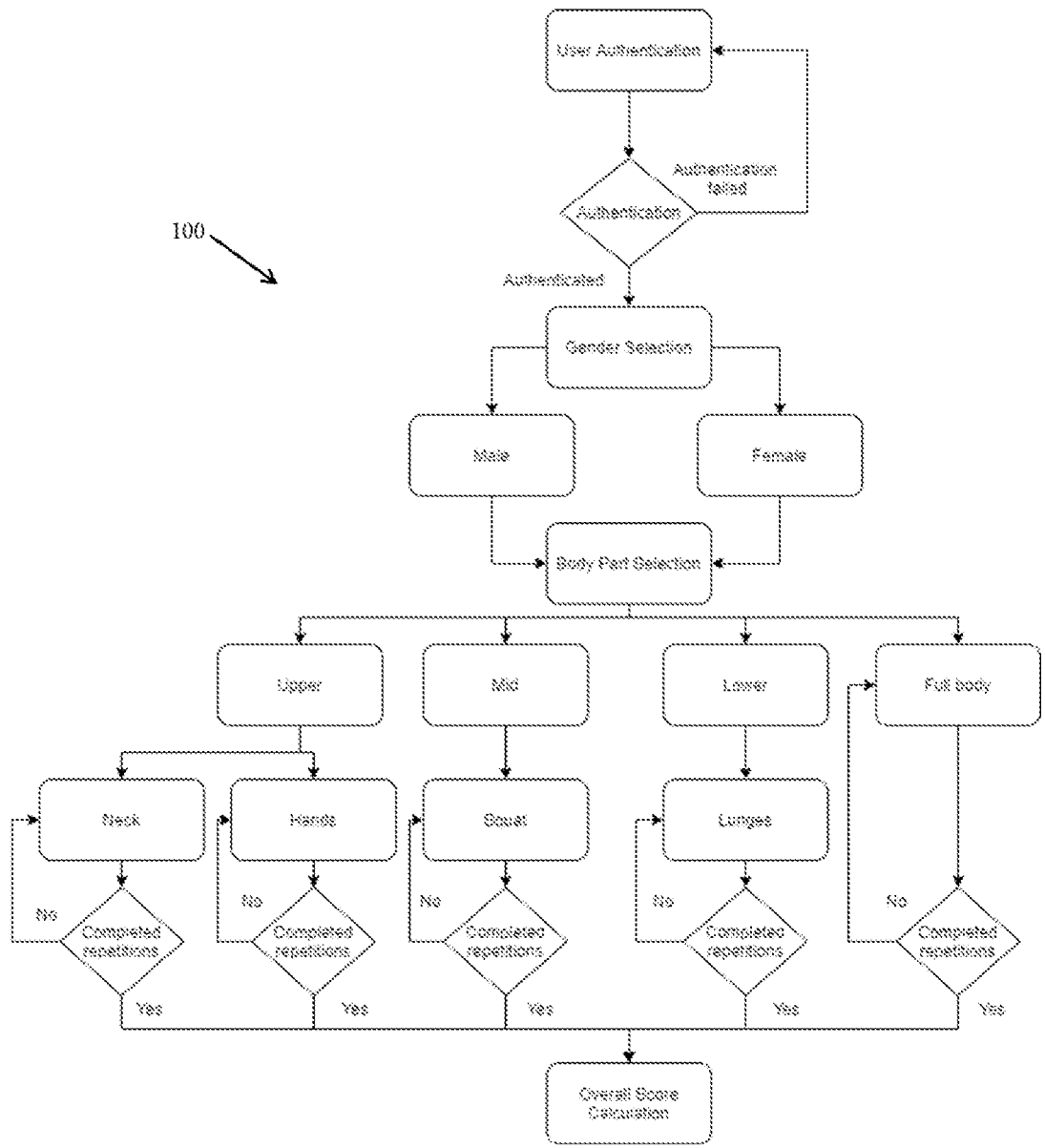
FIG. 2 illustrates a functional diagram of the system for assessing and improving wellness of person using body gestures according to some embodiments of the present disclosure.

According to an embodiment of the disclosure, a functional diagram of the system 100 is shown in FIG. 2. The system 100 comprises an application. The application is installed on a phone or any other computing device. As shown in FIG. 2, a user authentication is done in the application. Once the user is authenticated, then gender is selected for the person, followed by the selection of body part of the person performing the exercise. The selected body part could be one of an upper body part, lower body part, mid body part or full body. Depending on the selection of body part, the person performs one of the predefined exercises. The system 100 then checks whether the number of repetitions completed or not, and an overall score is calculated.

Figure 3:
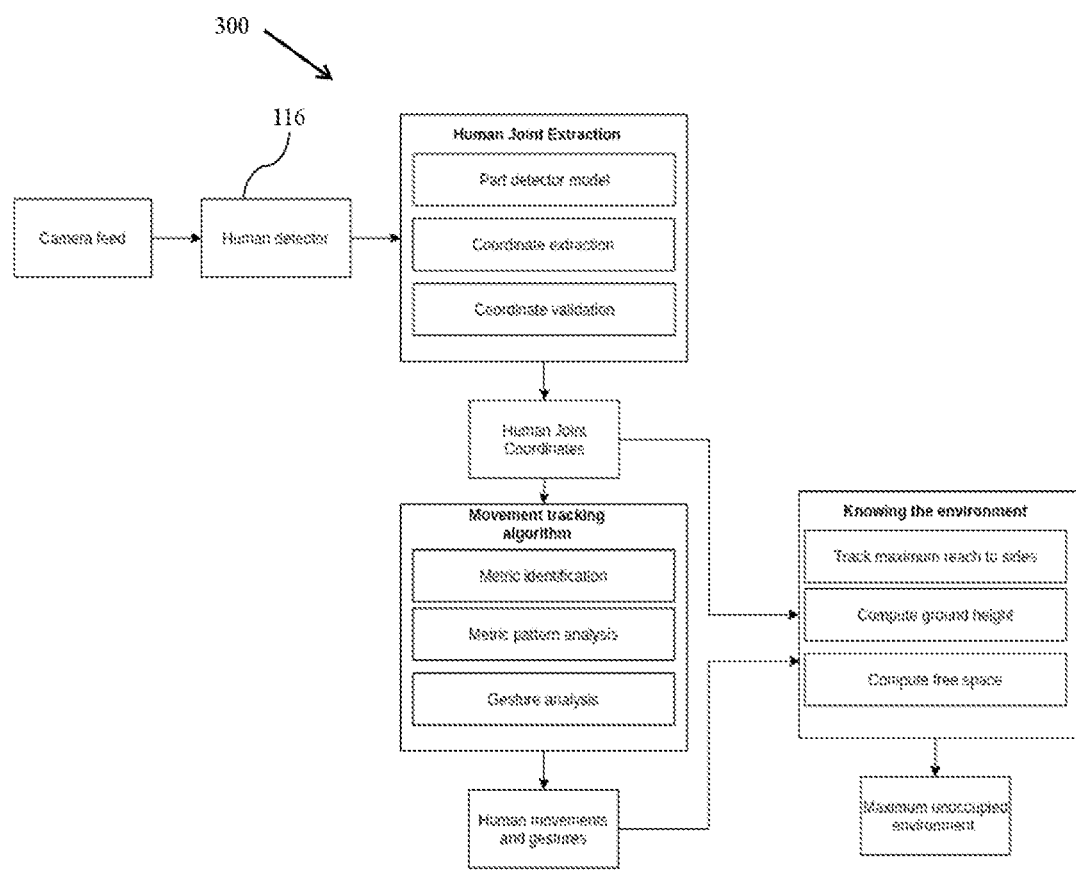
FIG. 3 illustrates a flow diagram illustrating the steps involved in identifying the environment surrounding the person according to some embodiment of the present disclosure.

According to an embodiment of the disclosure, a flow chart 300 for identification of the environment surrounding the person is shown in FIG. 3. The system 100 needs to be aware of the environment surrounding the person so that a set of appropriate exercise can be assigned to the person. The movements of the person are tracked using a camera 114 as shown in FIG. 1. The camera may be the camera present in a mobile phone, a standalone camera or a laptop camera. Using camera feed, the joint coordinates of the person with respect to the camera and the occupancy around the person for completing any task is computed.

To identify the environment of the person, the system 100 is configured to guide the person to perform a first set of exercises as a warmup session. During the first set of exercises tip joints are tracked to identify the maximum possible reach in any direction. The first set of exercises could be a combination of stretch and walk to know the limits. In case there are any obstacles in the environment, the system 100 is configured to alter the exercise based on the obstacles or features.

According to an embodiment of the disclosure, the system 100 is also configured to detect the presence of the person with the help of feed coming from the camera 114. Any frame without a human detection is eliminated from further processing. The image is the passed through a human part detector model 116, that has been trained to detect human body parts in an input image. The human part detector model 116 is built using transfer learning. The human part detector model 116 outputs a heatmap with the same size of the input image. The system 100 then computes the coordinates of the points of maximum joint detection from the heatmap. An additional layer is added at the output to ensure the joint coordinates have better accuracy and stays valid for the human. The additional layer is the classifier used on top of the joint detection model to identify the most valid joints using confidence measure returned by the model and a preset threshold confidence level.

According to an embodiment of the disclosure, the system 100 is configured to track the real time joint coordinates of the person while performing any exercise or task using a human joint extraction module 118. The real time joint coordinates are tracked by measuring a confidence. A minimal set of 17 joints have been identified. In an example, the status distances in the body of the person are identified, like distance between 2 shoulders, 2 eyes, 2 hip joints etc. Metrics available as the person moves keeps varying, so the system 100 is configured to dynamically identify the most confident joint from the model output to identify a movement identification metric. The most confident joint is identified based on a confidence value from the model output to identify a movement identification metric. The open-source convolutional model can predict 17 joint coordinates in image frame and their detection accuracy. The accuracy measure is taken as confidence measuring the corresponding joint coordinate. Further, a variation in rising or falling ramp signal of a Euclidean measure of the movement identification metric is measured, as the person moves forward or backward. The difference of step signals from the movement identification metric in adjacent frames is measured, as the person moves sideways. Variation in height is measured as an exponential growing or trailing sinusoid, as the person moves diagonally. And finally, the pattern of the movement identification metric is analyzed from frames to track the joint coordinates of the person. Thus, the output of this is awareness about the environment surrounding the person, this results in tracking of maximum reach to the sides of the person, computation of ground height and the computation of free space in the room.

Common gestures shown by person are collected and their positions are trained in a regression-based model. The model identifies the relation between joints for a gesture with respect to input frame resolution.

According to an embodiment of the disclosure, the system 100 is also configured to use trained data that was captured for standard joint variation for a human without any obstacle around him/her, validated using standard variations biologically defined for a human. The joint variations for the new person are predicted, then the obstacle bounds are applied around to reduce the expectation due to limitations faced by the person. Simulated data is then divided into 2 parts based on pattern change in joint coordinate measures. End coordinate measures of each section of the simulated data group are taken for validation. To track the person's motions, the real time joint coordinates are tracked and compared with the validation data generated, when the person performs the exercises. Based on this information the person is given timely alerts to complete in the required manner as he tries to complete the exercise in his/her own way.

Figure 4:
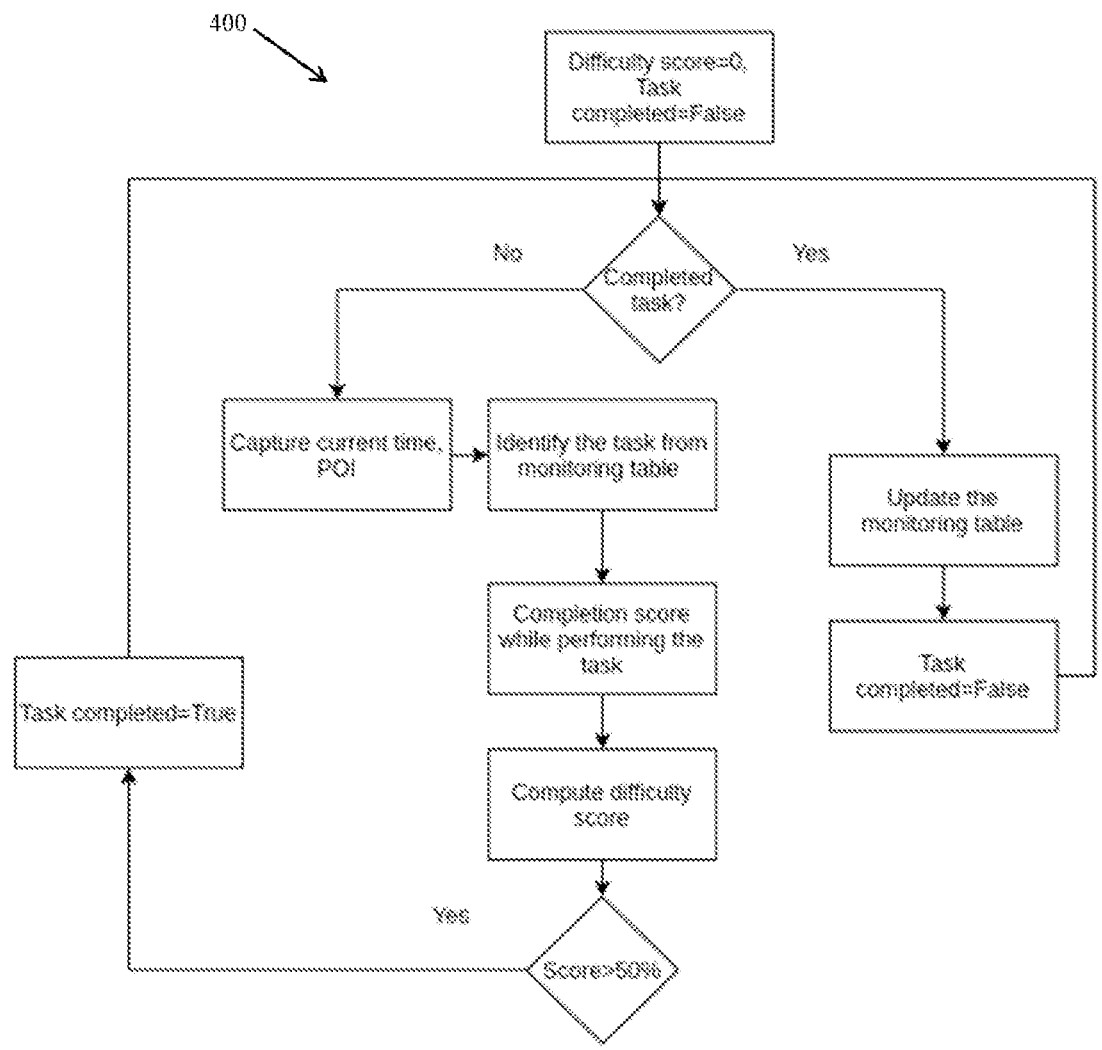
FIG. 4 is a flowchart showing the steps involved in the calculation of a completion score for the exercise according to some embodiment of the present disclosure.

According to an embodiment of the disclosure, the system 100 is configured to compute a percentage accuracy for the completion of the exercise performed by the person as shown in the flowchart 4 of FIG. 4. To calculate the percentage of achievement, the percentage closeness achieved around each validation point is computed. Considering all validation points the average completion is computed. This measure is later used to compute the completion score for the exercise. Thus, the completion score is represented using the formula given in equation (1)

Average completion score=$((V1*P1)+(P2*V2))/2$

Where,
V1=1, if first validation point reached, else 0.
P1=percentage closeness of first validation point
V2=1, if second validation point reached, else 0.
P2=percentage closeness of second validation point According to an embodiment of the disclosure, the system 100 is also configured to exhibit an adaptive nature for doing the exercises. The system 100 is configured to redefine the exercises for the person based on the physical dimensions of the person, physical structure of an object used by the person, changes in a position of the person and a task completion criterion pre-decided by the person.

The physical dimensions (S) of the person and the object, positions of the target objects (p) and the task completion criteria (c) are taken as the input. The physical characteristics of the person with environment constraints are fetched during the calibration process. Based on those values, the system 100 is configured to predict the best suitable object for the person in the current environment. The completion criteria based on the person characteristics are also adjusted. So, the adaptiveness of the system is measured by the product of physical characteristics of the person, position of the target object, completion rate and inverse of the time duration. Changes in the time inversely affects the changes in the system. If time increases the adaptiveness of the system will decreases and vice versa. it indicates the time that taken by the person to accomplish the given task.

It is known in that the failure of addition of the first two components affects the system. Even then, the system provides an adaptable environment based on task completion criteria changes.

$$da/dt=2S*f(p)*f(c)/t$$

$$S=u+o$$

$$f(p)=P+/-\Delta p$$

$$f(c)-C+/-\Delta c$$

where,
da/dt is the variation of adaptiveness over a small period t.
S is the factor denotes the physical nature of the objects.
u=physical dimensions of the person
o=physical nature of the object that chosen
f(p) is the rate function returns the changes in the position of the object over the given period.
f(c) is the rate function returns the changes in the completion criteria over a given period.
P is the initial position of the object
C is the initial task completion criteria.
$\Delta p$ is the change in the position of the object.
$\Delta c$ is the change in the task completion rate.

According to an embodiment of the disclosure, the system 100 if also configured to dynamic assign activity to the person based on the person's attributes. The system 100 dynamically allocates the exercise based on flexibility of the person, a time of use and requirements of the person. The system 100 continues to learn the data from logs to improve the performance over time. The data regarding, exercise type, completion score, time of action etc. is taken as the input. During an initial T-time (training time) of 10 active sessions the system 100 captures data and tries to make a model for the new user. To dynamically guide with the best exercises, following parameters need to be understood.

Difficulty level-For each user session log, difficulty level is computed. Difficulty level depends on the time taken to complete the task and the completion score achieved. Difficulty level, d a completion score/time taken. The proportionality constant for the above expression is a constant determined by the age of the user. Best exercise should be hard, but it should not be too difficult as it can lead to muscle cramps. So, the difficulty level is always maintained below a preset level.

Time of action-Effectiveness or percentage completion computed for the same exercise varies for the same person over time. This is due to the state of mind and variation in activity level. In the system 100, the completion scores for each time and the time of action in this part are also considered.

Best exercise=$f(t,d,c\_score)$, where t is the time of action
d is the difficulty level
c_score is the completion score.

A continuous learning model to predict the best exercise based on the known combinations is used. For a Part of Interest (POI), the list of simple, medium and hard tasks is identified. As a part of the solution, a monitoring table for a person with c_score, time of action, task name and difficulty level are prepared. For a person, first the monitoring table, the list of entries for the same POI is listed. From this resultant data, current time, and time of actions with a range of +/−1 hour is shortlisted. From the resultant data, the first task is assigned and its c_score is computed for every first trial in a day. Based on the difficulty level recorded, the system allocates the next task as a new task or one from a list with maximum recorded c_score with higher difficulty level. The algorithm continues to learn and grow the monitoring table for each task for every user. Reward for the current session is the completion score, it acts as a feedback to improve the system performance. Each day the level of difficulty or the completion score recorded can vary for a task. So, the monitoring table is timely updated with new data after extracting required insights from the data on a timely basis.

Figure 5:
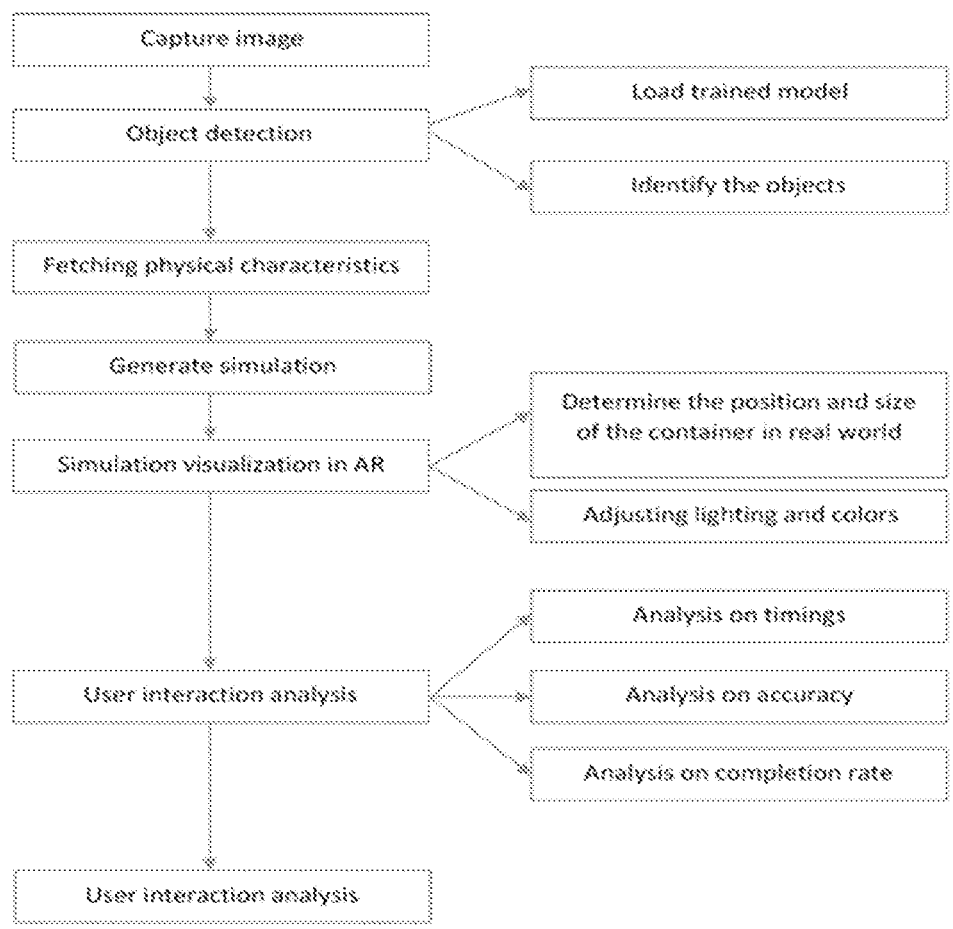
FIG. 5 shows a flowchart showing steps involved in object detection and dynamic activity assignment in augmented reality environment according to an embodiment of the present disclosure.

According to an embodiment of the disclosure, the system 100 is configured to detect the presence an object which is being held by the person while doing the exercise as shown in the flowchart 500 of FIG. 5. The system 100 is configured to automatically trigger the start of AR environment when the person picks the object, such as dumbbell, barbell, sticks, exercise ball, TheraBand etc.

The system 100 is using an object detection algorithm which is specifically trained for the person who is doing the exercise. Initially, the system 100 automatically captures the physical dimensions and the unique features of the person which were provided by the person. The person motions are periodically tracked and if the person picks up the object then the object detection model is invoked to find the object. After successful object detection, the system 100 provides a simulation which is having best suitable exercise for that person with the object.

The system 100 in the AR environment can also be explained with the help of an example. Assuming there are 2 users—a first user having height of 180 cm, weight of 90 kg and not able to move his left hand and doing all exercises well. A second user having height of 150 cm and weight of 67 kg and doing some exercise with good completion rate. Both users have picked dumbbell for doing their fitness routine. The system identifies the dumbbell and making simulation for doing the exercise. Even though both users are taking dumbbell for their exercise the physical dimension and previous history is taken into consideration. The exercises are defined for the first user will be hard with respect to previous one and float only on left hand side. But the exercise defined for the second user will be not that much hard and float over all places.

According to an embodiment of the disclosure, the system 100 is also configured to provide an immersive feeling by providing simulations in the AR environment as illustrated in the flow chart 500 of FIG. 5. So, the person gets a feel of the same happening in his environment. As already mentioned, the simulation is adaptable to the person. The visualization also done with person characteristics. The character in the visualization is having the person physical characteristics. For example, if the person having height of 180 cm and having difficulty to move left hand then the character appears in the simulation also having the same feature.

The system 100 internally captures images in each second to make object detection. Using the base image, the system 100 performs object detection from the pre-trained model. The pre-trained model contains a database of gym related objects that are used for training. With the help of measured physical characteristics of the person the system 100 creates a simulation of the exercise which is supported with the detected object. For example, if the detected object is dumbbell then the exercises are related to hands.

Further, the simulations are visualized in the AR environment. For that from the pre fetched environment data the system identifies the position and size of a container. The container is an AR place which is going to be used for placing the simulation in the AR space. The AR simulation is adaptable to the person's feelings and the environment constraints. The visualization part having the feature to adjust the lighting and color of visualization based on the environment constraints like if the room is dark and space is less, then the size of the simulation is compromised.

The system 100 is also configured to track the changes in the position of physical object. According to the transformation that are applied on the object is used to understand the person engagement in the exercise. Assume that dumbbell is raised 10 feet's, of course person did engagement on that. Based on the transformation on the detected object, the system is calculating timing, accuracy, and completion rate.

Figure 6:
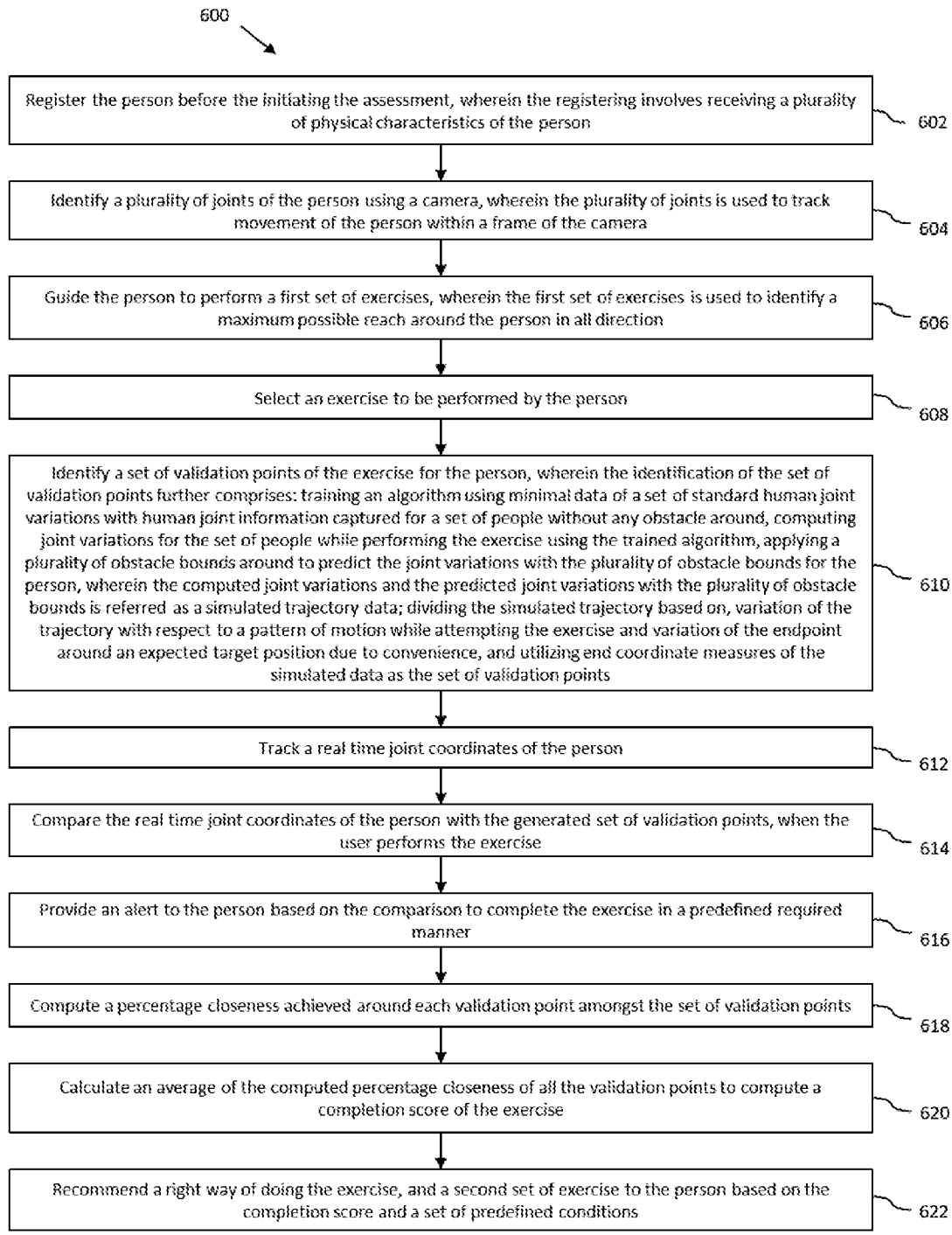
FIG. 6 shows flowchart illustrating steps involved in assessing and improving wellness of person using body gestures according to some embodiments of the present disclosure.

FIG. 6 illustrates an example flow chart of a method 600 for assessing and improving wellness of a person using body gestures, in accordance with an example embodiment of the present disclosure. The method 600 depicted in the flow chart may be executed by a system, for example, the system 100 of FIG. 1. In an example embodiment, the system 100 may be embodied in the computing device.

Operations of the flowchart, and combinations of operations in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 600 are described with help of system 100. However, the operations of the method 600 can be described and/or practiced by using any other system.

Initially at step 602 of the method 600, the person is registered in an application before the initiating the assessment. The application is normally installed in the mobile phone or a computer. The registering involves receiving a plurality of physical characteristics of the person such as weight, height etc.

At step 604 of the method 600, a plurality of joints of the person is identified using the camera. The plurality of joints is used to track movement of the person within the frame of the camera. The camera is present in front of the person. In an example a mobile phone camera, a standalone camera or a laptop camera can also be used. At step 606, the person is guided to perform a first set of exercises, wherein the first set of exercises is used to identify a maximum possible reach around the person in all direction. Further at step 608, the exercise is selected to be performed by the person.

At step 610 of the method 600, a set of validation points of the exercise for the person is identified. The identification of the set of validation points further comprises: training an algorithm using minimal data of a set of standard human joint variations with human joint information captured for a set of people without any obstacle around, computing joint variations for the set of people while performing the exercise using the trained algorithm, applying a plurality of obstacle bounds around to predict the joint variations with the plurality of obstacle bounds for the person, wherein the computed joint variations and the predicted joint variations with the plurality of obstacle bounds is referred as a simulated trajectory data, dividing the simulated trajectory based on, variation of the trajectory with respect to a pattern of motion while attempting the exercise and variation of the endpoint around an expected target position due to convenience, and utilizing end coordinate measures of the simulated data as the set of validation points.

At step 612 of the method 600, the real time joint coordinates of the person are tracked. At step 614, the real time joint coordinates of the person are then compared with the generated set of validation points, when the person performs the exercise.

At step 616 of the method 600, an alert is provided to the person based on the comparison to complete the exercise in a predefined required manner. At step 618, a percentage closeness achieved around each validation point amongst the set of validation points is computed. At step 620, an average of the computed percentage closeness of all the validation points is calculated to compute a completion score of the exercise.

And finally, at step 622 of the method 600, a right way of doing the exercise is recommended. In addition to that, a second set of exercises is also recommended to the person based on the completion score and a set of predefined conditions.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

In the present disclosure, the system 100 is built-in cost-effective manner and reduce the use of more device support. It is more flexible to run on any machine which support cross platform functionality. Moreover, the system 100 is 100% secure to use even though the system streams the video input it's not storing in the back end. Only using at real time to get the person posture and perform a matching algorithm based on that.

The embodiments of present disclosure herein address the problem of providing an effective solution to assess the wellness of the person without instructor's intervention or attaching any additional device to the person's body. The embodiment thus provides a method and system for assessing and improving wellness of a person using body gestures.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for assessing and improving wellness of a person using body gestures, the method comprising:
   registering the person before the initiating the assessment, via one or more hardware processors, wherein the registering involves receiving a plurality of physical characteristics of the person;
   identifying a plurality of joints of the person using a camera, wherein the plurality of joints is used to track movement of the person within a frame of the camera;
   guiding, via the one or more hardware processors, the person to perform a first set of exercises as a warmup session, wherein the first set of exercises is used to identify a maximum possible reach around the person in all direction and the first set of exercises is a combination of stretch and walk to know the limits and during the first set of exercises tip joints are tracked to identify the maximum possible reach in all direction;
   detecting, via the one or more hardware processors, presence of person in the frame of the camera in which an image is passed through a human part detector model that is trained to detect human body parts in the image and built using transfer learning, the human part detector model outputs a heatmap with same size of the image and computes coordinates of the points of maximum joint detection from the heatmap, wherein an additional layer is added at the output to ensure joint coordinates have better accuracy and stays valid for a human and the additional layer is a classifier used on top of a joint detection model to identify most valid joints;
   selecting, via the one or more hardware processors, an exercise to be performed by the person;
   identifying, via the one or more hardware processors, a set of validation points of the exercise for the person, wherein the identification of the set of validation points further comprises:
      training an algorithm using minimal data of a set of standard human joint variations with human joint information captured for a set of people without any obstacle around the person and validated using standard variation biologically defined for a human,
      computing joint variations for the set of people while performing the exercise using the trained algorithm,
      applying a plurality of obstacle bounds around to reduce expectation due to limitations faced by the person and to predict the joint variations with the plurality of obstacle bounds for the person, wherein the computed joint variations and the predicted joint variations with the plurality of obstacle bounds is referred as a simulated trajectory data,
      dividing the simulated trajectory data in to two parts based on, variation of the trajectory with respect to a pattern of motion while attempting the exercise and variation of the endpoint around an expected target position due to convenience, and
      utilizing end coordinate measures of the simulated data as the set of validation points;
   tracking, via the one or more hardware processors, a real time joint coordinates of the person to track motions of the person while performing the exercise;
   comparing, via the one or more hardware processors, the real time joint coordinates of the person with the generated set of validation points, when the person performs the exercise;
   providing, via one or more hardware processors, an alert to the person based on the comparison to complete the exercise in a predefined required manner;
   computing, via one or more hardware processors, a percentage closeness achieved around each validation point amongst the set of validation points;
   calculating, via one or more hardware processors, an average of the computed percentage closeness of all the validation points to compute a completion score of the exercise; and
   recommending, via the one or more hardware processors,
      a right way of doing the exercise, and
      a second set of exercises to the person based on the completion score and a set of predefined conditions, wherein a monitoring table for the person with completion score, time of action, task name, difficulty level are prepared, wherein for the person first the monitoring table and list of entries for a part of interest is listed, and continues to learn and grow the monitoring table for each task for every user and the monitoring table is timely updated with new data after extracting required insights from the data.

2. The method of claim 1 further comprising:
   identifying an object with the person using an object detection algorithm, wherein the object includes a dumbbell, a barbell, sticks, an exercise ball, a Thera-Band, wherein the object detection algorithm is specifically trained for the person performing the exercise and if the person picks up the object then the object detection algorithm is invoked to identify the object, wherein a system captures images in each second to make object detection from a pre-trained model containing database of gym related objects considered for training;
   capturing physical characteristics of the person; and
   providing a simulation to the person, wherein the simulation is showing suitable exercises being performed using the object, wherein the simulation is provided in an augmented reality (AR) view with automated adjustments based on environmental conditions and visualization in AR view is done with the physical characteristics of the person and a character in the visualization is having same physical characteristics of the person, wherein simulations are visualized in the AR view and from the environment, a system identifies position and size of a container in a AR space that is used for placing the simulation in the AR space and the visualization have feature to adjust lighting and color of the visualization based on the environment constraints like lighting of a room and space of the room.

3. The method of claim 1 further comprising providing physical dimensions of the person, physical structure of the plurality of objects including the dumbbell, the barbell, sticks, the exercise ball, the TheraBand, changes in the position of the person and task completion criteria as input.

4. The method of claim 1, wherein the movements comprise forward, backward, sideward, and diagonal movements.

5. The method of claim 1 wherein the step of tracking the real time joint coordinates of the person comprises:
 identifying distances between two organs or distance between two joints of the body of the person;
 dynamically identifying a most confident joint based on a confidence value from a model output to identify a movement identification metric, wherein the model provides a joint coordinate information from an input frame
 measuring a variation in rising or falling ramp signal of a Euclidean measure of the movement identification metric, as the person moves forward or backward,
 measuring the difference of step signals from the movement identification metric in adjacent frames, as the person moves sideways,
 measuring variation in height as an exponential growing or trailing sinusoid, as the person moves diagonally, and
 analyzing the pattern of the movement identification metric from frames to track the joint coordinates of the person and an output of analyzing the pattern of the movement is awareness about the environment surrounding the person resulting in tracking of maximum reach to sides of the person, computation of ground height and computation of free space in the room.

6. The method of claim 1 further comprising predicting the best exercise for the person.

7. A system for assessing and improving wellness of person using body gestures, the system comprises:
 an input/output interface for registering the person before the initiating the assessment, wherein the registering involves receiving a plurality of physical characteristics of the person;
 a camera for identifying a plurality of joints of the person, wherein the plurality of joints is used to track movement of the person within a frame of the camera;
 one or more hardware processors;
 a memory in communication with the one or more hardware processors, wherein the one or more first hardware processors are configured to execute programmed instructions stored in the one or more first memories, to:
  guide the person to perform a first set of exercises as a warmup session, wherein the first set of exercises is used to identify a maximum possible reach around the person in all direction and the first set of exercises is a combination of stretch and walk to know the limits and during the first set of exercises tip joints are tracked to identify the maximum possible reach in all direction;
  detect presence of person in the frame of the camera in which an image is passed through a human part detector model that is trained to detect human body parts in the image and built using transfer learning, the human part detector model outputs a heatmap with same size of the image and computes coordinates of the points of maximum joint detection from the heatmap, wherein an additional layer is added at the output to ensure joint coordinates have better accuracy and stays valid for a human and the additional layer is a classifier used on top of a joint detection model to identify most valid joints;
  select an exercise to be performed by the person;
  identify a set of validation points of the exercise for the person, wherein the identification of the set of validation points further comprises:
   training an algorithm using minimal data of a set of standard human joint variations with human joint information captured for a set of people without any obstacle around the person and validated using standard variation biologically defined for a human,
   computing joint variations for the set of people while performing the exercise using the trained algorithm,
   applying a plurality of obstacle bounds around to reduce expectation due to limitations faced by the person and predict the joint variations with the plurality of obstacle bounds for the person, wherein the computed joint variations and the predicted joint variations with the plurality of obstacle bounds is referred as a simulated trajectory data,
   dividing the simulated trajectory data in to two parts based on, variation of the trajectory with respect to a pattern of motion while attempting the exercise and variation of the endpoint around an expected target position due to convenience, and
   utilizing end coordinate measures of the simulated data as the set of validation points;
  track a real time joint coordinates of the person to track motions of the person while performing the exercise;
  compare the real time joint coordinates of the person with the generated set of validation points, when the person performs the exercise;
  provide an alert to the person based on the comparison to complete the exercise in a predefined required manner;
  compute a percentage closeness achieved around each validation point amongst the set of validation points;
  calculate an average of the computed percentage closeness of all the validation points to compute a completion score of the exercise; and
  recommend a right way of doing the exercise, and a second set of exercise to the person based on the completion score and a set of predefined conditions, wherein a monitoring table for the person with completion score, time of action, task name, difficulty level are prepared, wherein for the person first the monitoring table and list of entries for a part of interest is listed, and continues to learn and grow the monitoring table for each task for every user and the monitoring table is timely updated with new data after extracting required insights from the data.

8. The system of claim 7 further configured to:
 identify an object with the person using an object detection algorithm, wherein the object includes a dumbbell, a barbell, sticks, an exercise ball, a TheraBand, wherein the object detection algorithm is specifically trained for the person performing the exercise and if the person picks up the object then the object detection algorithm is invoked to identify the object, wherein a system captures images in each second to make object detection from a pre-trained model containing database of gym related objects considered for training;
capture physical characteristics of the person; and
provide a simulation to the person, wherein the simulation is showing suitable exercises being performed using the object, wherein the simulation is provided in an augmented reality (AR) view with automated adjustments based on environmental conditions and visualization in AR view is done with the physical characteristics of the person and a character in the visualization is having same physical characteristics of the person, wherein simulations are visualized in the AR view and from the environment, a system identifies position and size of a container in a AR space that is used for placing the simulation in the AR space and the visualization have feature to adjust lighting and color of the visualization based on the environment constraints like lighting of a room and space of the room.

9. The system of claim 7 further configured to provide physical dimensions of the person, physical structure of the plurality of objects including the dumbbell, the barbell, sticks, the exercise ball, the TheraBand, changes in the position and task completion criteria as input.

10. The system of claim 7 further configured to predict the best exercise for the person.

11. One or more non-transitory machine-readable information storage mediums comprising one or more instructions which when executed by one or more hardware processors cause:
registering the person before the initiating the assessment, wherein the registering involves receiving a plurality of physical characteristics of the person;
identifying a plurality of joints of the person using a camera, wherein the plurality of joints is used to track movement of the person within a frame of the camera;
guiding the person to perform a first set of exercises as a warmup session, wherein the first set of exercises is used to identify a maximum possible reach around the person in all direction and the first set of exercises is a combination of stretch and walk to know the limits and during the first set of exercises tip joints are tracked to identify the maximum possible reach in all direction;
detecting, via the one or more hardware processors, presence of person in the frame of the camera in which an image is passed through a human part detector model that is trained to detect human body parts in the image and built using transfer learning, the human part detector model outputs a heatmap with same size of the image and computes coordinates of the points of maximum joint detection from the heatmap, wherein an additional layer is added at the output to ensure joint coordinates have better accuracy and stays valid for a human and the additional layer is a classifier used on top of a joint detection model to identify most valid joints;
selecting an exercise to be performed by the person;
identifying a set of validation points of the exercise for the person, wherein the identification of the set of validation points further comprises:
training an algorithm using minimal data of a set of standard human joint variations with human joint information captured for a set of people without any obstacle around the person and validated using standard variation biologically defined for a human,
computing joint variations for the set of people while performing the exercise using the trained algorithm,
applying a plurality of obstacle bounds around to reduce expectation due to limitations faced by the person and to predict the joint variations with the plurality of obstacle bounds for the person, wherein the computed joint variations and the predicted joint variations with the plurality of obstacle bounds is referred as a simulated trajectory data,
dividing the simulated trajectory data in to two parts based on, variation of the trajectory with respect to a pattern of motion while attempting the exercise and variation of the endpoint around an expected target position due to convenience, and
utilizing end coordinate measures of the simulated data as the set of validation points;
tracking a real time joint coordinates of the person to track motions of the person while performing the exercise;
comparing the real time joint coordinates of the person with the generated set of validation points, when the person performs the exercise;
providing an alert to the person based on the comparison to complete the exercise in a predefined required manner;
computing a percentage closeness achieved around each validation point amongst the set of validation points;
calculating an average of the computed percentage closeness of all the validation points to compute a completion score of the exercise; and
recommending
a right way of doing the exercise, and
a second set of exercises to the person based on the completion score and a set of predefined conditions, wherein a monitoring table for the person with completion score, time of action, task name, difficulty level are prepared, wherein for the person first the monitoring table and list of entries for a part of interest is listed, and continues to learn and grow the monitoring table for each task for every user and the monitoring table is timely updated with new data after extracting required insights from the data.

* * * * *